United States Patent

Makovec et al.

[11] Patent Number: 6,075,033
[45] Date of Patent: Jun. 13, 2000

[54] ANTHRANILIC ACID DIAMIDES DERIVATIVES, THEIR PREPARATION AND PHARMACEUTICAL USE AS ANTI-GASTRIN AGENTS

[75] Inventors: Francesco Makovec, Monza; Walter Peris, Milan; Lucio C. Rovati; Luigi A. Rovati, both of Monza, all of Italy

[73] Assignee: Rotta Research Laboratorium S.p.A, Monza, Italy

[21] Appl. No.: 09/214,229

[22] PCT Filed: Jul. 2, 1997

[86] PCT No.: PCT/EP97/03361

§ 371 Date: Dec. 31, 1998

§ 102(e) Date: Dec. 31, 1998

[87] PCT Pub. No.: WO98/00404

PCT Pub. Date: Jan. 8, 1998

[30] Foreign Application Priority Data

Jul. 30, 1996 [IT] Italy .................... TO96A0564

[51] Int. Cl.⁷ .................................................. A61K 31/44
[52] U.S. Cl. ........................................ 514/278; 546/16
[58] Field of Search ................................. 514/278; 546/16

[56] References Cited

U.S. PATENT DOCUMENTS

| 5,500,430 | 3/1996 | Makovec et al. | 514/278 |
| 5,587,479 | 12/1996 | Makovec et al. | 544/70 |
| 5,723,494 | 3/1998 | Makovec et al. | 514/563 |

FOREIGN PATENT DOCUMENTS

| WO 92 10479A | 6/1992 | WIPO |
| WO 93 21172A | 10/1993 | WIPO |
| WO 94 20454A | 9/1994 | WIPO |
| WO 95 07261A | 3/1995 | WIPO |
| WO 97 02248A | 1/1997 | WIPO |

*Primary Examiner*—Amelia Owens
*Attorney, Agent, or Firm*—Sughrue, Mion, Zinn, Macpeak & Seas, PLLC

[57] ABSTRACT

Compounds which can be represented by general formula (I) indicated below,

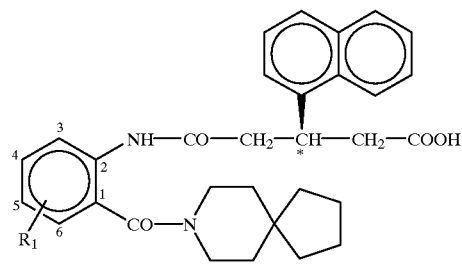

and in which the anthranilic acid aromatic ring may be mono- or di-substituted by the $R_1$ group which can be selected independently from hydrogen, methyl and chloro, and in which the substituents at the chiral center (marked with an asterik in formula (I)) have the R (Rectus) configuration.

10 Claims, No Drawings

ANTHRANILIC ACID DIAMIDES DERIVATIVES, THEIR PREPARATION AND PHARMACEUTICAL USE AS ANTI-GASTRIN AGENTS

The subject of the present invention is new, original derivatives of anthranilic acid which can be represented by the general formula (I) indicated below

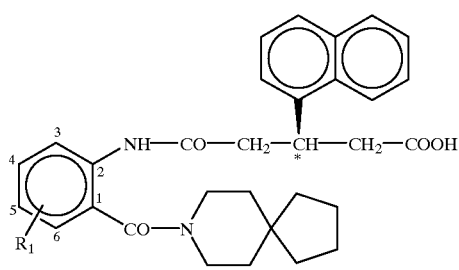

(I)

and in which the anthranilic acid aromatic ring may be mono- or di-substituted with the $R_1$ group which can be selected independently from hydrogen, methyl and chloro, and in which the substituents at the chiral centre (marked with an asterisk in formula (I)) have the R (Rectus) configuration.

The anthranilic acid aromatic ring is preferably di-substituted with the methyl group in positions 3, 5 or with the chloro group in position 3 and the methyl group in position 5.

The compounds of the present invention have been found to be potent receptor antagonists of gastrin at the peripheral level, that is, at the level of the gastro-intestinal system, and potent receptor antagonists of cholecystokinin (CCK) at the level of the central nervous system (CCK-B-antagonists).

It can therefore be considered that they may be usable to advantage in the treatment of various diseases in man connected with imbalances in the physiological levels of gastrin and of CCK or of other bioactive polypeptides correlated therewith, both at the level of the gastro-intestinal system and at the level of the central nervous system (CNS), of the sense organs, or of other organs or systems in which these bioactive peptides play a physiological or pathological role. For example, advantageous use of these compounds can thus be predicted for the treatment, at the gastro-intestinal level, of diseases connected with disorders of motility and of trophism of the mucous membrane such as, for example, gastritis, peptic ulcers, colitis or certain gastro-intestinal tumours sustained by gastrin or polypeptide hormones correlated therewith and, at the level of the CNS, for the treatment of psychic disorders such as, for example, anxiety, panic attacks, psychosis, such as, for example, schizophrenia, depression, anorexia, etc. Pharmaceutical forms of the compounds of the invention such as, for example, tablets, capsules, suspensions, solutions, suppositories or patches, may be prepared in accordance with conventional techniques and may be administered by oral, parenteral, or rectal routes, through the skin or the mucous membrane, or by other means suitable for achieving the therapeutic effect such as, for example, solid preparations for oral use with delayed action which permit controlled release of the active substance over time.

The active ingredient is typically administered to the patient with a reference dose variable from 0.01 to 10 mg/kg of body weight per dose. For parenteral administration, the use of a water-soluble salt of the compounds of the invention such as the sodium salt or another non-toxic and pharmaceutically acceptable salt is preferable. Substances commonly used in pharmacology as excipients, binders, flavourings, dispersers, colourings, humectants, etc., may be used as inactive ingredients.

The method for the preparation of the derivatives of the invention is an enantio-selective method which enables the derivatives of formula (I) to be obtained in the optically active R (Rectus) form which is the pharmacologically active enantiometric form.

The method comprises the following steps:

a) reacting isatoic anhydride, suitably substituted with $R_1$, in which $R_1$ has the meaning given above, with azaspiro[4.5]decane hydrochloride in the presence of a tertiary base such as triethylamine, in an inert anhydrous solvent at a temperature of between 20° C. and the boiling point of the solvent, to give benzamides of formula (V), b) reacting 3-(1-naphthyl) glutaric anhydride containing one prochiral carbon atom with methanol, preferably in a slight excess, in an inert solvent, preferably toluene, at ambient temperature, for a period of between 8 and 24 hours, in the presence of a semi-catalytic quantity of an asymmetric tertiary base, preferably cinchonine or quinidine to give the monomethyl ester of (R)-3-(1-naphthyl) glutaric acid of formula (IV), c) reacting the methyl ester of formula (IV) with thionyl chloride with boiling for a period of between 1 and 4 hours to give the corresponding chloride of formula (III), d) reacting the benzamide of formula (V) with the chloride of formula (III) in the presence of two moles of a tertiary base, preferably triethylamine, in an inert anhydrous solvent, at a temperature of between 20° C. and 80° C., for a period of between 4 and 24 hours, to give the amido-esters of formula (II), in which $R_1$ has the meaning given above, e) hydrolysing the compounds of formula (II) dissolved in an inert solvent or in a mixture of inert solvents such as, for example, methanol and dichloromethane with an aqueous solution of sodium hydroxide at ambient temperature for a period of between 12 and 72 hours. After evaporation of the solvents and acidification of the oily residue, recovering, from the reaction mass, by conventional methods, the diamides of anthranilic acid of formula (I) in which $R_1$ has the meaning given above and with the chiral centre in the R (Rectus) configuration.

The series of steps of the method according to the invention is illustrated as a whole in the following scheme (Scheme 1):

Scheme 1
Step 1
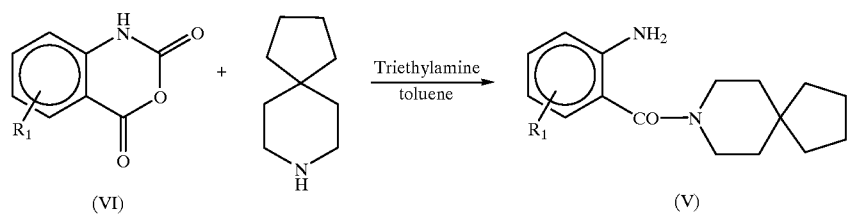
Step 2
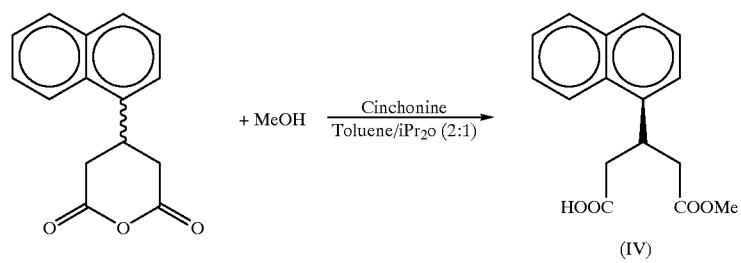
Step 3
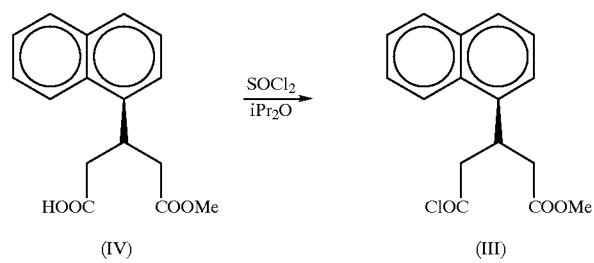
Step 4
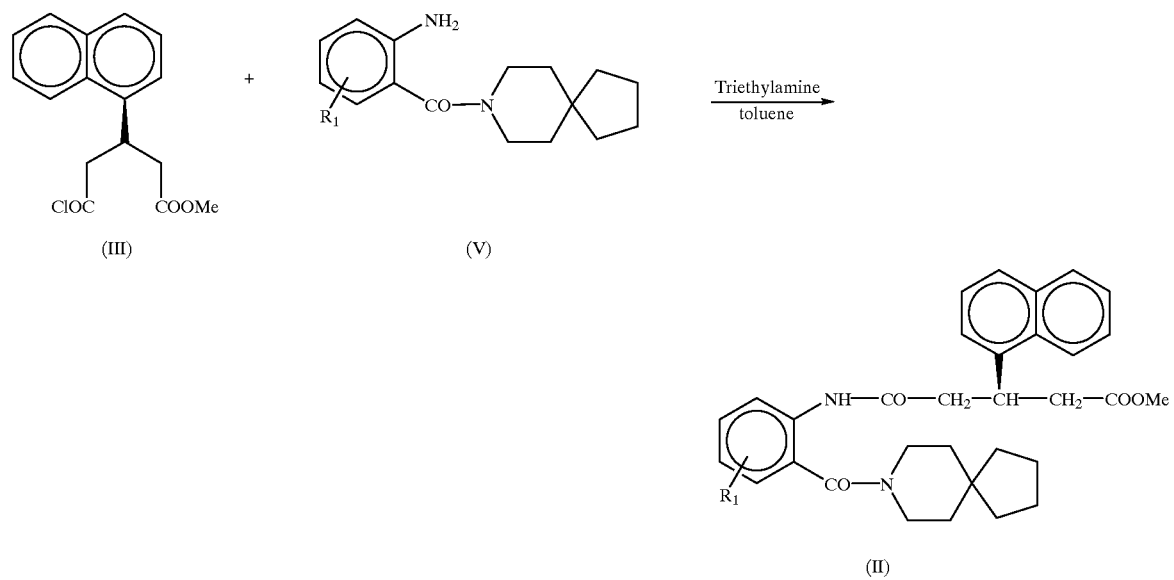

Step 5

(II) →[1N NaOH / CH₂Cl₂/MeOH (8:5)] (I)

-continued

The following examples are given to illustrate the invention further.

EXAMPLE 1
Preparation of 2-amino-3,5-dimethyl(azaspiro[4.5]decan-8-yl)benzamide (V)

60 g of 3,5-dimethylisatoic anhydride (0.134 moles), 55.1 g of azaspiro[4.5]decane hydrochloride (0.314 moles) and 87.5 ml of triethylamine (0.628 moles) were added to 500 ml of toluene. The resulting solution was heated for 2 hours with refluxing and was then cooled and the organic phase was washed with a potassium bisulphate solution (pH 4) and then with dilute sodium carbonate and finally to neutrality with $H_2O$. After dehydration and evaporation of the solvent, a solid residue was obtained and was taken up with petroleum ether and filtered. After drying at 50° C. under vacuum, 69 g of product was obtained.

Formula $C_{18}H_{26}N_2O$. Yield (77%); TLC (chloroform/ethyl acetate 7:3) rf 0.54. M.P. 91° C.

All of the intermediate compounds of formula (V) were synthesized with the use of the same method (see Scheme 1, step 1).

EXAMPLE 2
Preparation of (R)-3-(1-naphthyl) Glutaric Acid Monomethyl Ester (IV)

50 g of 3-(1-naphthyl) glutaric anhydride (0.208 moles), 14.7 g of cinchonine (0.05 moles), and 10 ml of methanol (0.25 moles) were added to 1 liter of toluene. The mixture was left to react at ambient temperature for 24 hours with stirring. The solution was washed with dilute hydrochloric acid and to neutrality with water. After dehydration and evaporation of the solvent, the residue was taken up with 150 ml of isopropyl ether. After two hours, the precipitate formed, which was an approximately 50% mixture of (R) isomer and (S) isomer, was filtered out and discarded. The titrated ethereal solution containing the ether-soluble (R) enantiomer was used as it was in the next step without further purification. 0.13 moles of product was obtained, determined by titration of the ethereal solution but not isolated.

Formula $C_{16}H_{16}O_4$. Yield 62%; TLC (isoamyl alcohol-acetone-$H_2O$ 5:2:2) Rf. 0.65 (N.B.: 3-(1-naphthyl) glutaric acid has Rf. 0.52 in the same eluent).

EXAMPLE 3
Preparation of the Chloride of (R)-3-(1-naphthyl) Glutaric Acid Monomethyl Ester (III)

8.7 ml (0.12 moles) of thionyl chloride was added to an ethereal solution containing 0.10 moles of compound (IV) prepared as described in Example 2. The resulting solution was heated for 3 hours with refluxing and was then cooled and the solvents were evaporated under vacuum. The oily residue was dissolved in 100 ml of toluene and used as it was in the next step without further purification.

Formula $C_{16}H_{15}ClO_3$. Yield 100% (purely theoretical).

EXAMPLE 4
Preparation of the Methyl Ester of 3-(R)-(1-naphthyl)-5-[1'-[carbamoyl(8-azaspiro[4.5]decan-8-yl]3'-5'-dimethyl-2'-phenylaminol]-5-oxopentanoic Acid (II)

28 ml (0.2 moles) of triethylamine was added to 200 ml of a toluene solution of 28.6 g (0.1 moles) of amine (V) prepared as described in Example 1, and a toluene solution of 0.1 moles of the chloride (III) prepared as described in Example 3 was then added slowly so as not to exceed 60° C.

Upon completion of the addition, the mixture was heated to 60° C. for a further 5 hours. The mixture was cooled, the precipitate (triethylamine×HCl) was discarded by filtration, the solvent was evaporated under vacuum and the oily residue was taken up with ethyl ether and filtered.

After drying at 50° C. under vacuum, 47.6 g of product was obtained.

Formula $C_{34}H_{40}N_2O_4$. Yield (88%); TLC (chloroform/ethyl acetate 7:3) Rf. 0.40 M.P. 149° C.; Rotatory power $[a]^{21}_D=39°$ (1% in methanol).

All of the intermediate compounds of formula (II) were synthesized with the use of the same method (see Scheme 1, step 4).

EXAMPLE 5
Preparation of 3-(R)-(1-naphthyl)-5-[1'-carbamoyl(8-azaspiro[4.5]decan-8-yl)]-3',5'-dimethyl-2'-phenylamino]-5-oxopentanoic Acid (Compound 1)

75 g (0.139 moles) of methyl ester (II) prepared as described in Example 4 was dissolved in 1 liter of a 1:1 methanol/methylene chloride mixture. 150 ml of 1N NaOH (0.15 moles) was added and the mixture was left to react with stirring at ambient temperature for 48 hours. The solvents were evaporated under vacuum and the oily residue was taken up with 300 ml of a methylene chloride/ethyl acetate mixture (4:1). This mixture was left for 12 hours with stirring and 12 g of precipitate constituted by a 1:1 mixture of the (1-R) and (1-S) enantiomers was filtered off. The filtration solvent was washed with 200 ml of 1N HCl and then to neutrality with $H_2O$. After dehydration and evaporation of the solvents under vacuum, a semi-solid residue was obtained and was crystallized by treatment with isopropyl ether. After drying at 50° C. under vacuum, 57 g of product was obtained.

M.P. 182° C. (crystallized from ethyl acetate); Formula $C_{33}H_{38}N_2O_4$. Yield 78%; HPLC: rt 12.4 min.

HPLC conditions: Adsorbosphere C18 column, length 25 cm, eluent $KH_2PO_4$ 0.01M/methanol 25/75 (pH 2.85), flow 0.9 ml/min, UV at 224 nm.

Rotatory power $[a]^{21}_D=31.5°$ (methanol/chloroform 75/25).

Optical purity [EC=capillary electrophoresis]=97%.

Analytical conditions for EC analysis: non-coated fused silica capillary 82.7 cm column; capillary diameter 50 mm; temperature 35.0° C.; voltage 22 kV (266 V/cm); UV detector at 225 nm; sample: 0.3 mg/ml in 500 ml of methanol+20 mM $Na_2B_4O_7$ at 5 ml; volume injected about 13 nl (equal to about 3.8 ng); elution buffer: 60 nM $Na_2B_4O_7$+50 mM ursodeoxycholic acid at pH 9.2; migration time: 17.0 minutes against 17.3 of the S enantiomer.

All of the compounds of formula I were synthesized with the use of the method described by way of example for Compound 1 (see Scheme 1, step 5).

Some derivatives of formula (I) thus obtained in accordance with the invention are given in Table 1 below with some identifying chemical and physical characteristics.

For the synthesis of the S series enantiomers which are not the subject of the invention but are given by way of example in Table 1 and which were prepared for comparative purposes, the method described in Scheme 1 was used with the sole exception of Step 2, in which quinine was used instead of cinchonine as the asymmetric synthesis inductor.

brane content corresponding to about 300 mcg of proteins/ml incubated with a final concentration of 0.2 nM of radioligand.

The results obtained for some of the compounds of the invention are shown in Table 2 in which the $IC_{50}$, that is, the concentration (in micromoles/liter) of the antagonist which can displace 50% of the [3-H](pBC264)CCK-7 from the receptor, is given.

TABLE 2

Inhibition of the binding of ($^3$H)-[pBC264]CCK-7 to guinea-pig cortex membranes

| Compound | $IC_{50} \times 10^{-9}$ M |
|---|---|
| 1 | 5.1 |
| 2 | 2.5 |
| 3 | 4.7 |
| 4 | 54.7 |
| 5 | 22.9 |
| Pentagastrin | 3.0 |

Compounds 4 and 5 which are the (S) enantiomers of compounds 1 and 2, respectively, and are therefore not subjects of the invention, have been given by way of example and, on average, are 10 times less active than the corresponding (R) derivatives.

It can be seen from the data given in Table 2 that some of the compounds of the invention are extremely potent inhibi-

TABLE 1

Compounds of formula (I)

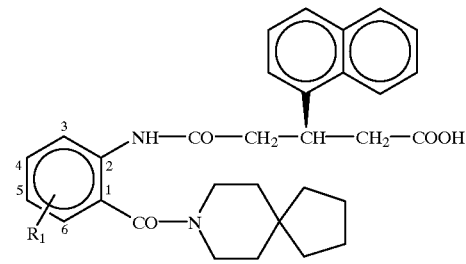

| Compound | Formula | $R_1$ | Melting Point (° C.) | HPLC (rt in minutes) | Rotatory power $[\alpha]^{21}_D$ (solvent) | Capillary electrophoresis (rt in minutes) |
|---|---|---|---|---|---|---|
| 1 | $C_{33}H_{38}N_2O_4$ | 3,5-dimethyl | 182 | 12.4 | 31.5° (MeOH/CHCl$_3$ 3:1) | 17.0 |
| 2 | $C_{32}H_{35}ClN_2O_4$ | 3-chloro, 5-methyl | 205 | 12.8 | 29.5° (MeOH) | 17.9 |
| 3 | $C_{33}H_{32}Cl_2N_2O_4$ | 3,5-dichloro | 187 | 17.5 | 11.2° (CHCl$_3$) | 19.0 |
| 4* | $C_{33}H_{38}N_2O_4$ | 3,5-dimethyl | 180 | 12.4 | −29.6° (MeOH/CHCl$_3$ 3:1) | 17.3 |
| 5* | $C_{32}H_{35}ClN_2O_4$ | 3-chloro, 5-methyl | 202 | 12.8 | −27.0° (MeOH) | 18.3 |

(*) Compounds 4 and 5 are enantiomers of the S (sinister) configuration and are given for comparison.

DESCRIPTION OF PHARMACOLOGICAL ACTIVITY

1) Anti-cholecystokinin (anti CCK-B) Activity in vitro

[3-H][pBC264]CCK-7 was used to evaluate the ability of the compounds of the invention to interact with the central CCK-B receptor. This ligand has been show: to be selective for the CCK-B receptors since it has an affinity for the cortex (CCK-B) receptors 3 logarithmic orders of magnitude greater than for those of the pancreas (CCK-A) in the guinea pig (C. Durieux et al. Eur. J. Pharmacol. 168 (1989 page 269].

Cerebral cortexes of male albino guinea pigs were therefore used with the method given above, to obtain a memtors the binding of [pBC264]CCK-7 to guinea-pig cortex membrane receptors, showing that, in this experimental model, it has the same affinity for the central CCK receptor (CCK$_B$) as the specific agonist, pentagastrin.

2) Anti-gastrin Activity (peripheral) in vitro in Rabbit Gastric Mucous-membrane Cells The parietal cells of the gastric mucous membrane are responsible for the secretion of HCl. They have specific membrane receptors which can be activated by gastrin and which have been defined as type B (CCK-B) gastrin or cholecystokinin receptors.

Since it has been observed that the activation of CCK-B receptors by gastrin leads to an increase in the level of cytosol calcium ions, a technique of measurement of the increase in intracellular calcium induced by gastrin in the presence and in the absence of the compounds of the invention was used as an indication of the anti-gastrin activity of the compounds.

Suspensions ($0.8 \times 10^6$/ml) of rabbit gastric mucous-membrane cells were prepared by conventional techniques with the use of collagenase and pronase as digestive enzymes; the basal $[Ca^{2+}]_i$ values, that is, those reached after stimulation of the cellular system, were estimated in accordance with Grynkiewicz et al [J. Biol. Chem. 260 (1985), 3440]. In the control samples, the cells were stimulated with $5 \times 10_{-8}$ gastrin, whereas in the samples in which the effect of the compounds of the invention was evaluated, the cells were incubated with these compounds before stimulation with gastrin. The results are expressed as percentage increments of $[Ca^{2+}]_i$ with reference to the control value. The anti-gastrin activity of the compounds was expressed as the $IC_{50}$ value, that is, the concentration (in micromoles/liter) at which the response to the stimulus induced by gastrin was reduced by 50%. The results thus obtained for some compounds of the invention are given in Table 3.

TABLE 3

Inhibition of the increase in cytosol calcium induced by gastrin in rabbit gastric mucous-membrane cells

| Compound | $IC_{50} \times 10^{-9}$ M |
| --- | --- |
| 1 | 4.3 |
| 2 | 3.5 |
| 3 | 8.8 |
| 4 | 68.8 |
| 5 | 82.0 |

It can be seen from the data given in Table 3 that some of the compounds of the invention are extremely potent inhibitors of the increase in cytosol calcium induced by gastrin in rabbit gastric mucous-membrane cells. The peripheral anti-gastrin activity essentially accords well with the anti-gastrin activity obtained centrally by the binding investigations described above in Table 2. In fact, compounds 1–3 were also active in a nanomolar range of concentrations in this case. In general, the compounds of the invention show anti-gastrin activity in this model at concentrations about 20 times lower than those obtained with the corresponding (S) series enantiomers (that is, compounds 4–5).

3) Anti-cholecystokinin (anti-CCK-A) Activity

In order to check the hypothesis that the compounds of the invention are specific CCK-B antagonists, they were also tested for any CCK-A antagonistic activity. Guinea-pig gall bladder stimulated in vitro by CCK-8 by the method described by Makovec et al [(Arzneim.Forsch./Drug. Res. 35 (7), 1048–1051 (1985)] was used as the experimental model.

None of the compounds tested was found to posses CCK-A antagonistic activity more potent than $1 \times 10^{-6}$ M.

It can be concluded from a comparison of these activities with the CCK-B antagonistic activity shown above in Table 2 that the compounds of the invention are specific antagonists for the CCK-B receptor, the most potent compounds such as, for example, compound 1, exhibiting an affinity at least 1000 times greater for the gastrin receptor (CCK-B) than for the cholecystokinin receptor (CCK-A).

4) Anxiolytic Activity

Amongst the possible therapeutic activities of the compounds of the invention on the central nervous system connected with imbalances in the physiological neuron levels of gastrin or other peptides correlated therewith, their potential anxiolytic activity seems particularly interesting.

An important role has in fact recently been postulated for the central CCK-B receptor in anxiety. This is in accordance with studies also carried out in man which have shown that the central CCK-B mechanisms have an important function in the mediation of panic attacks (Bradwejn, J. et al; J. Psychopharmacology 6 (1992), 345]. In order to confirm this hypothesis, the anxiolytic activity of some of the most potent CCK-B antagonists of the invention was evaluated with the use of the "elevated plus-maze" method in the rat, carried out in accordance with Pellow et al [J. of Neurosc. Meth. 14 (1985), 149–167]. A labyrinth in which the length of the cross limbs was 45 cm was used and was placed at a height of 70 cm from the ground. In this experimental model, a compound having anxiolytic activity produces a % increase in the time spent in the open limbs and a % increase in the number of entries to the open limbs.

The results obtained are shown in Table 4 below, in which the activities obtained with various doses of compound 1 administered by an intraperitoneal route (IP) in comparison with a group of animals treated with physiological solution by the same route.

TABLE 4

Anxiolytic activity in the rat in the "Plus Maze" test

| Compounds | Dose mg/kg I.P. | No. of animals | Entries open limbs/total entries (%) | % effect Vs controls | Time open limbs/ total time (%) | % effect Vs controls |
| --- | --- | --- | --- | --- | --- | --- |
| Controls | — | 12 | 31.8 | — | 21.7 | — |
| Compound 1 | 0.03 | 12 | 42.2 | 32.6 | 27.5 | 26.4 |
| " | 0.3 | 12 | 41.8 | 31.5 | 32.8(*) | 50.9 |
| " | 3.0 | 12 | 40.2 | 26.3 | 30.1 | 38.5 |

(*): Duncan test: $p < 0.05$ vs control group

It can be noted from an examination of Table 4 that compound 1 shows anxiolytic activity.

In fact, it can be seen that, within the dose range of 0.03–3 mg/kg I.P., the compound increases the % of entries to the open limbs over the number of total entries in comparison with the controls.

At the middle dose used, that is, 0.3 mg/kg I.P., compound 1 also increases the % of time spent in the open limbs; this increase is significant in comparison with the control group of animals treated solely with physiological solution.

The anxiolytic response shown by compound 1 has a bell-shaped curve which is typical of compounds active on the central nervous system.

What is claimed is:

1. Compounds which can be represented by the general formula (I) indicated below:

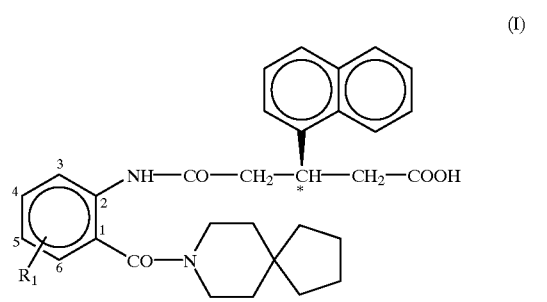

and in which the anthranilic acid aromatic ring may be mono- or di-substituted with the $R_1$ group which can be selected independently from hydrogen, methyl and chloro, and in which the substituents at the chiral centre marked with an asterisk in formula (I) have the R configuration.

2. A compound according to claim 1 of general formula (I) in which the anthranilic acid aromatic ring is di-substituted with the methyl group in positions 3 and 5 and in which the stereochemistry of the chiral central marked in (I) is R.

3. A compound according to claim 1 of general formula (I) in which the anthranilic acid aromatic ring is substituted with a chloro group in position 3 and with a methyl group in position 5, and in which the stereochemistry of the chiral centre marked in (I) is R.

4. A pharmaceutical preparation comprising, as an active substance, at least one of the compounds according to claim 1 or a pharmaceutically acceptable salt thereof.

5. A pharmaceutical preparation according to claim 4 for use in treatment related to its activity against ulcers.

6. A pharmaceutical preparation according to claim 4 for use in the treatment of complaints of the gastro-intestinal system.

7. A pharmaceutical preparation according to claim 4 for use in the treatment of tumors sustained by gastrin, by cholecystokinin and by other bioactive polypeptides correlated therewith.

8. A pharmaceutical preparation according to claim 4 for the treatment of pathological conditions of the SNC linked with imbalances in the physiological neuron levels of gastrin or of other bioactive polypeptides correlated therewith or with other pathological condetions of the sense organs correlated with the mechanesm of the action of the compounds.

9. A pharmaceutical preparation according to claim 4, also comprising pharmaceutically acceptable inactive ingredients selected from the group of ingredients acceptable for the various pharmaceutical forms or ingredients which facilitate absorption through the skin or through the mucous membranes, and which permit controlled release of the active substance over time.

10. A method for the preparation of a derivative of general formula (I) in which $R_1$ has the meaning given above in claim 1 and in which the substituents at the chiral centre marked with an asterisk have the R configuration, comprising the steps of:

a) reacting isatoic anhydride of formula (VI):

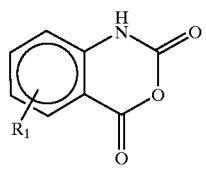

(VI)

in which $R_1$ has the meaning given above, with azaspiroa[4.5]decane hydro chloride in the presence of a tertiary base in an inert anhydrous solvent at a temperature between 20° C. and the boiling point of the solvent to give benzamides of formula (V),

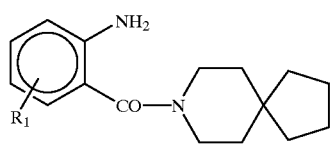

(V)

b) reacting 3-(1-naphthyl) glutaric anhydride containing one prochiral carbon atom with methanol in an inert solvent, at ambient temperature for a period of between 8 and 24 hours, in the presence of a semi-catalytic quantity of an asymmetric tertiary base to give the monomethyl ester of (R)-3-(1-naphthyl) glutaric acid, c) reacting the monomethyl ester of (R)-3-(1-naphthyl) glutaric acid with thionyl chloride with boiling for a period of between 1 and 4 hours to give the corresponding chloride, d) reacting benzamide of formula (V) in which $R_1$ has the meaning given above with the chloride of (R)-3-(1-naphthyl) glutaric acid monomethyl ester in the presence of two moles of a tertiary base in an anhydrous solvent, at a temperature of between 20° C. and 80° C. for a period of between 4 and 24 hours, to give diamido-esters of formula (II) in which $R_1$ has the meaning given above, e) hydrolysing the diamido-esters of formula (II)

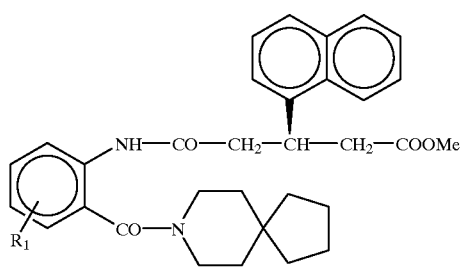

(II)

in which $R_1$ has the meaning given above, dissolved in an an inert solvent or in a mixture of inert solvents with an aqueous solution of sodium hydroxide at ambient temperature for a period of between 12 and 72 hours; after evaporation of the solvents and acidification of the oily residue, recovering from the reaction mass by conventional methods the diamides of anthranilic acid of formula (I) in which $R_1$ has the meaning given above and in which the substituents at the chiral centre marked with an asterisk have the R configuration

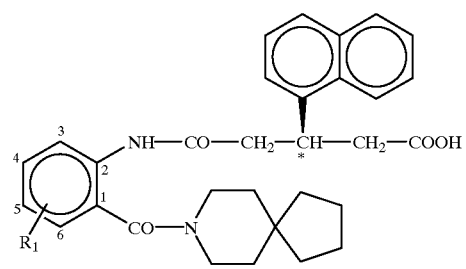

(I)

* * * * *

UNITED STATES PATENT AND TRADEMARK OFFICE
CERTIFICATE OF CORRECTION

PATENT NO. : 6,075,033
DATED : June 13, 2000
INVENTOR(S) : Francesco Makovec et al.

It is certified that error appears in the above-identified patent and that said Letters Patent is hereby corrected as shown below:

Under Item [22] Filed,
Please change "Jul. 2, 1997" to -- Jul. 2, 1996 --.

Under Item [30], Foreign Application Priority Data,
Please change "Jul. 30, 1996" to -- June 26, 1997 --.

Signed and Sealed this

Fourth Day of December, 2001

Attest:

NICHOLAS P. GODICI
Attesting Officer
Acting Director of the United States Patent and Trademark Office